US009617311B2

(12) United States Patent
Tsao et al.

(10) Patent No.: US 9,617,311 B2
(45) Date of Patent: *Apr. 11, 2017

(54) USE OF PEDF-DERIVED POLYPEPTIDES FOR PROMOTING STEM CELLS PROLIFERATION AND WOUND HEALING

(71) Applicant: Mackay Memorial Hospital, Taipei (TW)

(72) Inventors: Yeou-Ping Tsao, Taipei (TW); Tsung-Chuan Ho, Taipei City (TW)

(73) Assignee: Mackay Memorial Hospital, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/656,107

(22) Filed: Mar. 12, 2015

(65) Prior Publication Data

US 2015/0183832 A1    Jul. 2, 2015

Related U.S. Application Data

(62) Division of application No. 13/428,996, filed on Mar. 23, 2012, now Pat. No. 9,051,547.

(30) Foreign Application Priority Data

Mar. 23, 2011 (TW) .............................. 100109945 A

(51) Int. Cl.
| | |
|---|---|
| *C07K 14/00* | (2006.01) |
| *A61K 38/18* | (2006.01) |
| *C12N 5/079* | (2010.01) |
| *C12N 5/071* | (2010.01) |
| *C07K 7/08* | (2006.01) |
| *C12N 5/0797* | (2010.01) |

(52) U.S. Cl.
CPC .............. *C07K 14/00* (2013.01); *A61K 38/18* (2013.01); *C07K 7/08* (2013.01); *C12N 5/0621* (2013.01); *C12N 5/0623* (2013.01); *C12N 5/0628* (2013.01); *C12N 2501/10* (2013.01); *C12N 2501/998* (2013.01)

(58) Field of Classification Search
None
See application file for complete search history.

(56) References Cited

U.S. PATENT DOCUMENTS

2009/0069241 A1* 3/2009 Barnstable ........... C07K 14/811
514/13.3
2010/0047212 A1  2/2010 Farinas Gomez et al.

FOREIGN PATENT DOCUMENTS

| WO | WO 2005/041887 A2 | 5/2005 |
| WO | WO 2007/095350 A2 | 8/2007 |

OTHER PUBLICATIONS

J. Chmielowiec et al., "c-Met is essential for wound healing in the skin" *The Journal of Cell Biology*, vol. 177, No. 1, Apr. 9, 2007 pp. 151-162.
W. Li et al., "Niche regulation of corneal epithelial stem cells at the limbus" *Cell Research* (2007) 17; pp. 26-36.
H. J. Snippert et al., "Lgr6 Marks Stem Cells in the Hair Follicle That Generate All Cell Lineages of the Skin" *Science*, vol. 327, Mar. 12, 2010 pp. 1385-1389.
E. A. Blazejewska et al., "Corneal Limbal Microenvironment Can Indue Transdifferentiation of Hair Follicle Stem Cells into Corneal Epithelial-like Cells" *Stem Cells* 2009; 27, pp. 642-652.
H. Wang et al., "Importin 13 Serves as a Potential Market for Corneal Epithelial Progenitor Cells" *Stem Cells*, 2009, 27; pp. 2516-2526.
O. Stojadinovic et al., "Hair Cycling and Wound Healing: To Pluck or not to Pluck?" *Journal of Investigative Dermatology* (2011), vol. 131, pp. 292-294.
S. V. Petersen et al., "Pigment-epithelium-derived factor (PEDF) occurs at a physiologically relevant concentration in human blood; purification and characterization" *Biochem. J.* (2003) 374, pp. 199-206.
L. Takacs et al., "Stem Cells of the Adult Cornea: From Cytometric Markers to Therapeutic Applications" *Cytometry* Part A, 75A: Dec. 2, 2008, pp. 54-66.
M. Ito et al., "Stem cells in the hair follicle bulge contribute to wound repair but not to homeostasis of the epidermis" *Nature Medicine* vol. 11, No. 12, Dec. 2005 pp. 1351-1354.
C. Blanpain "Skin regeneration and repair" *Nature*, vol. 464, Apr. 1, 2010, pp. 686-687.
C. C. Cheng et al., "The growth-promoting effect of KGF on limbal epithelial cells is mediated by upregulation of $\Delta$Np63$\alpha$ through the p38 pathway" *Journal of Cell Science*, 122, Sep. 26, 2009, pp. 4473-4480.
S. Burman et al., "Cultivated limbal stem cell transplatation for ocular surface reconstruction" *Clinical Ophthalmology* 2008:2(3), pp. 489-502.
Amaral et al., "Effects of Human Recombinant PEDF Protein and PEDFDerived Peptide 34-mer on Choroidal Neovascularization," *Invest Ophthalmol Vis Sci.* 2010, Mar. 2010, pp. 1318-1326.
De Marzo et al., "Chapter 71: PEDF Promotes Retinal Neurosphere Formation and Expansion In Vitro," *Hormonal Carcinogenesis V (Advances in Experimental Medicine and Biology)*, Springer Pub., pp. 621-630 (Sep. 23, 2008).
Elahy et al., "The Emerging Role of PEDF in Stem Cell Biology," *Journal of Biomedicine and Biotechnology*, vol. 2012, Article ID 239091, pp. 1-6 (2012).

* cited by examiner

*Primary Examiner* — Lianko Garyu
(74) *Attorney, Agent, or Firm* — Muncy, Geissler, Olds & Lowe, P.C.

(57) ABSTRACT

Disclosed herein is a synthetic peptide, which has an amino acid sequence that has 20-39 amino acid residues. The synthetic peptide has at least 80% amino acid sequence identity to SEQ ID NO: 1, and includes at least 20 consecutive residues that has at least 90% amino acid sequence identity to residues 11-30 of SEQ ID NO: 1. Also disclosed herein are compositions containing the synthetic peptide and applications thereof. According to various embodiments of the present disclosure, the synthetic peptide is useful in promoting stem cells proliferation or wound healing.

14 Claims, 12 Drawing Sheets
(11 of 12 Drawing Sheet(s) Filed in Color)

Day 4 post-wounding

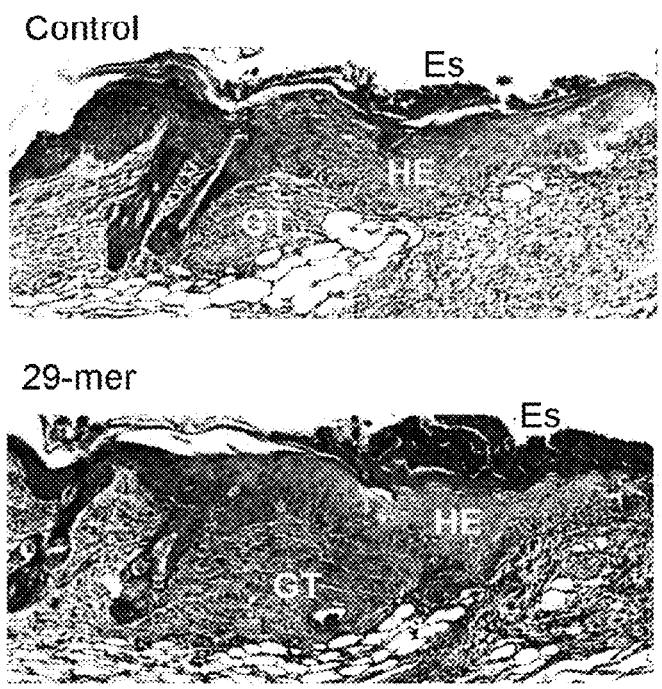
Fig. 7C
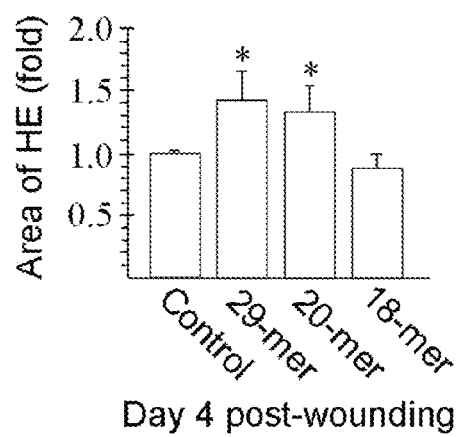
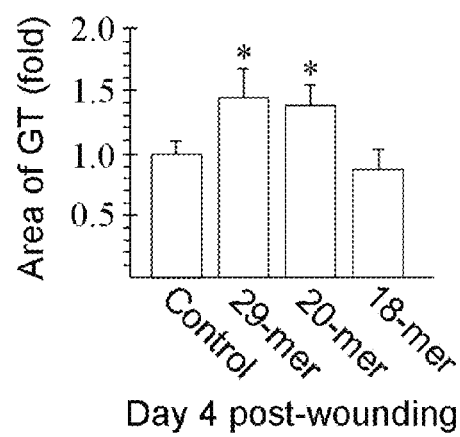
Fig. 7D
Fig. 7E

Day 7 post-wounding

Day 4 post-wounding

USE OF PEDF-DERIVED POLYPEPTIDES FOR PROMOTING STEM CELLS PROLIFERATION AND WOUND HEALING

CROSS-REFERENCE TO RELATED APPLICATION

This application is a divisional application of U.S. patent application Ser. No. 13/428,996, filed Mar. 23, 2013, which claims priority to Taiwan application NO: 100109945, filed Mar. 23, 2011, the entireties of which are incorporated herein by reference.

BACKGROUND OF THE INVENTION

1. Field of the Invention

The present disclosure relates to stem cell proliferation. More particularly, the disclosed invention relates to the proliferation of limbal epithelial stem cells (LSCs) or hair follicle stem cells (HFSCs).

2. Description of Related Art

Stem cells are associated with the formation, repair, and maintenance of tissues during embryogenesis and injuries and aging in the adults. Stem cells are unique in their self-renewal capacity and differentiation potential. The capacity of self-renewal enables these stem cells to make more copies thereof, whereas differentiation potential allows them to differentiate into multiple or all the germ lineages. These properties are collectively defined as the "stemness" of stem cells.

Mammalian stems cells are broadly categorized into embryonic stem cells and adult stem cells. Embryonic stem cells are derived from the inner cell mass of blastocysts which is formed in the early embryogenesis of mammals. These embryonic stem cells are totipotent, which means they may give rise to all the tissues of a complete organism. Embryonic stem cells can be maintained in culture as undifferentiated cell lines or induced to differentiate into many different lineages, and therefore, they have been widely used in fields of molecular biology and medicine. However, one drawback of maintaining embryonic stem cells in culture is their tendency to differentiate spontaneously and thereby lose their proliferation capacity over time. Many tissues in adult animals have been shown to contain reservoirs of stem cells, which are called "adult stem cells." Adult stem cells, in comparison with to embryonic stem cells, have a more restricted differentiation capacity, and are usually lineage-specific. These adult stems cells are often associated with the repair and maintenance of tissues. For example, bone marrow stem cells may migrate to various tissues after injuries, while tissue stem cells located outside the bone marrow may repair the tissues in which they reside.

Limbus anatomically locates between cornea and sclera at ocular surface. The basal layer of limbal epithelium is enriched with a special cell population, named limbal epithelial stem cells (LSCs). The cornea is a stratified squamous epithelium with a rapid turnover property that maintains corneal transparency and visual acuity. The renewal of corneal epithelium is supported by the transient amplifying cells (TACs) who are generated by asymmetric division of LSCs. In addition, LSCs are normally slow cycling cells, but activated by corneal wounding that enable corneal damage repaired.

Partial or total loss or dysfunction of LSCs (clinical termed LSC deficiency) leads to corneal neovascularization, recurrent erosions, stromal scarring, ulceration, thereby causing vision loss. LSC deficiency may arise following injuries including chemical or thermal burns and through diseases such as aniridia, chronic infection (e.g., trachoma), mycotic keratitis, and Stevens Johnson syndrome. Currently, transplantation of the ex vivo expanded limbal epithelial sheet has become the most widely used therapy for LSC deficiency. This therapeutic approach generally involves placing a small limbal biopsy removed from either the patient or a donor on transplantable carriers such as denuded human amniotic membrane to support limbal cells migrating out from the biopsy and outgrowth to form a limbal-like epithelial sheet. In addition, enzymatically isolating the limbal cells from limbal tissue and their expansion by suspension culture systems contributes to decrease the LSCs spontaneously differentiation. The failure of limbal transplantation is often arising from the depletion of LSCs in culture. Accordingly, it is desirable to effectively expand the quantity of LSCs in vitro or ex vivo before the transplantation.

Adult mammalian epidermis consists of the hair follicles (HFs), the sebaceous glands (SGs), and the interfollicular epidermis. The homeostasis of each of these three epithelial compartments is supported by their own stem cell (SC) population. Hair follicle stem cells (HFSCs) reside in the hair follicle bulge; they are multipotent and have the capacity to give rise to all epidermal lineages. HFSCs are predominantly responsible for reconstituted HFs during homeostasis rather than responsible for the formation of epidermis. However, after skin wounding, HFSCs contribute to interfollicular epidermal repair. Yet, the in vivo proliferation of HFSCs following the injuries is not fast enough, and may slowdown the wound healing process. Moreover, in the event of large amount of skin loss, such as those resulted from infection, surgical excision, and burn, there may be insufficient available HFSCs to participate in wound healing.

In view of the foregoing, there exists a need in the art to provide a method of promoting the proliferation of stem cells, which in turn may promote wound healing.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based, at least, on the finding that synthetic peptides derived from pigment epithelium-derived factor (PEDF) may promote the proliferation of limbal epithelial stem cells or hair follicle stem cells, and thereby promote wound healing processes respectively associated with these two types of stem cells. The PEDF-derived synthetic peptides of this invention are, therefore, useful as an agent or a medicament for treating wounds.

Accordingly, in one aspect, the present disclosure is directed to a synthetic peptide for promoting stem cells proliferation.

According to embodiments of the present disclosure, the synthetic peptide is 20-39 amino acid residues in length, and has an amino acid sequence that is at least 80% identical to SEQ ID NO: 1. Also, the amino acid sequence comprises at least 20 consecutive residues, which is at least 90% identical to residues 11-30 of SEQ ID NO: 1, such that the synthetic peptide is useful in promoting the proliferation of limbal epithelial stem cells or hair follicle stem cells. Non-limiting examples of such synthetic peptides include those having an amino acid sequence of SEQ ID NO: 1, SEQ ID NO: 2, SEQ ID NO: 3, SEQ ID NO: 5, SEQ ID NO: 7, or SEQ ID NO: 8.

In another aspect, the present disclosure is directed to a composition for promoting stem cells proliferation. This composition is suitable for promoting the in vivo, ex vivo, or in vitro proliferation of stem cells, in particular, limbal epithelial stem cells and hair follicle stem cells.

According to one embodiment of the present disclosure, the composition comprises a synthetic peptide according to any of the above-mentioned aspect/embodiments, and the synthetic peptide is present in an effective amount sufficient to promote the stem cell proliferation. The composition also comprises a carrier for the synthetic peptide. In the case of in vitro proliferation, the carrier may be a powdered culture medium suitable for culturing the stem cells. According to embodiments of the present disclosure, the synthetic peptide is present in the culture medium in an amount of about 1-100 nM, and preferably, about 25-50 nM. In the case of in vivo proliferation, the carrier may be a pharmaceutically acceptable carrier suitable for administering to a living mammal, including human. For example, the pharmaceutically acceptable carrier may be any of a liquid, gel, cream, ointment, adhesive, amniotic membrane, skin substitute, artificial skin, or skin equivalents.

In yet another aspect, the present invention is directed to a method for promoting stem cells proliferation.

According to one embodiment, the method comprises treating the stem cells with an effective amount of the synthetic peptide according to any of the above-mentioned aspect/embodiments, thereby promoting the stem cells to proliferate. In various embodiments, the stem cells are proliferated in vivo, ex vivo, or in vitro.

In still another aspect, the present invention is directed to a method for promoting healing of a corneal or an epithelial wound in a subject. The subject may be any animal classified as a mammal, including human.

In one embodiment, the method comprises administering to the subject a therapeutically effective amount of the composition according to the above-mentioned aspect/embodiments of the present disclosure so as to promote stem cells associated with the corneal or epithelial wound of the subject to proliferate. In practice, the composition may be administered via topical administration, subconjunctival injection, subcutaneous injection, or intradermal injection.

According to some embodiments, the corneal wound is caused by pterygium; recurrent corneal erosion; limbal deficiency caused by dry eye or drug toxicity; corneal damage caused by chemical or thermal burn, or herpes virus; keratopathy induced by contact lens or radiation; corneal lesions induced by Stevens Johnson Syndrome, aniridia, limbal tumors, ocular cicatricial pemphigoid (OCP), limbal deficiency-induced corneal neovascularization, or diabetes-induced difficulty of corneal wound healing.

According to other embodiments, the epithelial wound is caused by surgical excision, skin ulcer derived from infection, chemical or thermal burn, donor site of full thickness and split thickness skin graft, bedsore, and ischemic necrosis, or diabetes-induced and age-induced difficulty of skin surface wound healing.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

The present description will be better understood from the following detailed description read in light of the accompanying drawings, where:

FIGS. 7A to 7E provide quantification of wound healing at day 4. FIG. 7A provides representative photographs from skin specimen stained by Masson trichrome (original magnification, ×100) and the 29-mer and 20-mer treated wound showed better wound healing. Arrowheads (▼) and arrows (↓) denote initial wound margins and the foremost tips of the hyperproliferative epithelium (HE; red color), respectively. Data are representative of 10-16 wounds (2 wounds per mouse) in each group. *P<0.02 versus control wound. FIG. 7B is a histogram illustrating the residual epithelial defect (%) in mice from each treatment group; only sections of the middle of the wounds were used for quantification. Data are shown as mean±SE. FIG. 7C provides representative photographs of wound edge. GT: granulation tissue (blue color); Es: eschar (deep-red). 29-mer treated wound showed thicker HE. FIGS. 7D and 7E are histograms providing quantifications of the areas of HE and GT using Adobe Photoshop CS3 10.0. *P<0.02 versus control wound.

FIG. 8A provides representative photographs from skin specimen stained by Masson trichrome (original magnification, ×100) and the 29-mer, Mo 29-mer, and 20-mer treated wound showed better wound healing. Arrowheads (▼) and arrows (↓) denote initial wound margins and the foremost tips of the hyperproliferative epithelium, respectively. FIG. 8B is a histogram illustrating the residual epithelial defect (%) in mice from each treatment group; only sections of the middle of the wounds were used for quantification. Data are shown as mean±SE. *P<0.05 versus control wound.

FIG. 9A provides photographs in which specimens were immunehistologically stained with BrdU to observe DNA replication (deep brown color) and counterstained with hematoxylin to observe nuclei. Representative photograph showed cell replication mainly at basal layer of HE tissue as indicated by arrow (↓). (Original magnification, ×200). FIG. 9B is a histogram illustrating numbers of BrdU-positive cells at basal layer of HE tissue. A labeling index (%) was computed as the number of labeled cells divided by the total number of cells at basal layer of HE tissue. *P<0.05 versus control wound.

FIG. 10A provides photographs in which specimens were immunehistologically stained with Lgr6 to observe HFSC-derived cells at HE tissue and counterstained with hematoxylin to observe nuclei. Original magnification, ×400. FIG. 10B presents photographs in which sections of 20-mer ointment-treated wound were stained with BrdU- and Lgr6-specific antibodies. Lgr6 is expressed in the cell nucleus as confirmed by Hoechst 33258 counterstaining.

DESCRIPTION

Figure 1A:
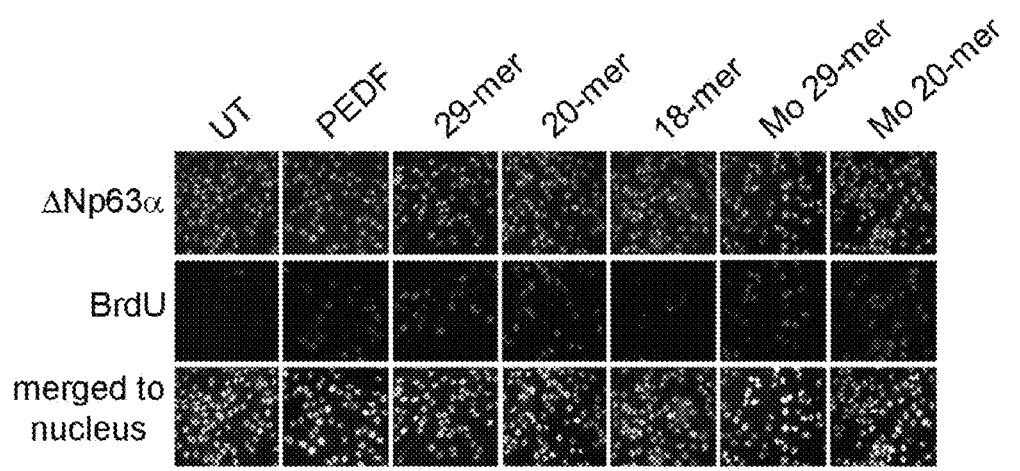
FIG. 1A provides immunofluorescence microscopy photographs and FIG. 1B is a histogram, and together, they illustrate the in vitro proliferation of LSCs from treatment groups according to one example of the present disclosure. LSC proliferation was determined by BrdU labeling for 2 hours. LSCs ($\Delta$Np63$\alpha$, green) and BrdU (red) were detected by immunofluorescence microscopy (original magnification, ×400). Ten randomly selected fields in each group were photographed, and the percentage of BrdU and $\Delta$Np63$\alpha$-double positive cells (pale pink) per total $\Delta$Np63$\alpha$-positive cells was calculated. *$P<0.002$ versus untreated cells.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the entire application (including the specification, examples, and appended claims) are collected here. Unless otherwise defined herein, scientific and technical terminologies employed in the present disclosure shall have the meanings that are commonly understood and used by one of ordinary skill in the related art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "peptide" denotes a polymer of amino acid residues. By the term "synthetic peptide" as used herein, it is meant a peptide which does not comprise an entire naturally occurring protein molecule. The peptide is "synthetic" in that it may be produced by human intervention using such techniques as chemical synthesis, recombinant genetic techniques, or fragmentation of whole antigen or the like. Throughout the present disclosure, the positions of any specified amino acid residues within a peptide are numbered starting from the N terminus of the peptide.

The term "stem cell" as used herein, refers to a cell that retains the capacity, under certain circumstances, to proliferate without substantially differentiating; as well as the capacity or potential, under particular circumstances, to differentiate to a more specialized or differentiated phenotype. As discussed hereinabove, the present disclosure is particularly related to two adult tissue stem cells, i.e., limbal epithelial stem cells and hair follicle stem cells. Tissue stem cells are located in sites called niches, which differ among various tissues. For example, limbal epithelial stem cells reside preferentially in the basal layer of peripheral cornea in the limbal zone, whereas hair follicle stem cells reside in the hair follicle bulge.

As used herein, "proliferating" and "proliferation" refers to an increase in the number of cells in a population by means of cell division.

The term "promote" or "promoting" is meant to refer to a positive alteration; in particular a statistically significant positive alteration. The positive alteration means an increase of at least 10% as compared to a reference level.

"Percentage (%) amino acid sequence identity" with respect to the synthetic polypeptide sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation. The carrier can be in the form of a solid, semi-solid, or liquid diluent, cream or a capsule.

As used herein, the terms "treat" or "treating" or "treatment" refer to preventative (e.g., prophylactic), curative or palliative treatment. The term "treating" as used herein refers to application or administration of the composition of the present disclosure to a subject, who has a medical condition, a symptom of the condition, a disease or disorder secondary to the condition, or a predisposition toward the condition, with the purpose to partially or completely alleviate, ameliorate, relieve, delay onset of, inhibit progression of, reduce severity of, and/or reduce incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable.

The term "effective amount" as used herein refers to the quantity of a component which is sufficient to yield a desired response. The term "therapeutically effective amount" as used herein refers to the amount of therapeutically agent of pharmaceutical composition to result in a desired "effective treatment" as defined hereinabove. The specific therapeutically effective amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed. A therapeutically effective amount is also one in which any toxic or detrimental effects of the compound or composition are outweighed by the therapeutically beneficial effects.

The term "subject" refers to a mammal including the human species that is treatable with the compositions and/or methods of the present invention. The term "subject" is intended to refer to both the male and female gender unless one gender is specifically indicated.

Pigment epithelium-derived factor (PEDF) is a multifunctional secreted protein that has anti-angiogenic, anti-tumorigenic, and neurotrophic functions. Human PEDF protein is a secreted protein of roughly 50 kDa size and 418 amino acids in length. A 34-mer fragment (residues 44-77) and a 44-mer fragment (residues 78-121) of PEDF have been identified to have anti-angiogenic and neurotrophic properties, respectively.

The full-length human PEDF molecule has been previously reported as a factor for enhancing symmetrical self-renewal of neural stem cells (US Patent Publication NO: 2010/0047212 by Gomez et al.). Said application also disclosed a C-ter PEDF (amino acids 195-400) which was unable to promote self-renewal of neural stem cells. Their results implied that a domain within the first 194 N-terminal amino acids may be necessary for self-renewal of neural stem cells; however, no specific N-terminal fragments were described or tested. Gomez et al. further taught that the C-ter PEDF was capable of competitively inhibiting the self-renewal effect of the full length PEDF on neural stem cells, which implied that the C-ter PEDF must also play a role in the self-renewal activity of the native PEDF. Nevertheless, Gomez et al. did not explicitly or implicitly taught or suggested any specific PEDF fragment that is capable of enhancing symmetrical self-renewal of neural stem cells. In addition, no effects of PEDF (full-length or fragment thereof) on other types or sources of stem cell, other than neural stem cells, have been disclosed or tested. Given the diversity of conditions of the niches in which various tissue stem cells reside and the complexity of the inducing and regulation of symmetrical and asymmetrical stem cell proliferations, Gomez et al. provided no direction or guidance regarding stem cell types that may be promoted to proliferate under the action of the full-length PEDF molecule.

The present disclosure is based, at least, on the finding that synthetic peptides derived from PEDF may promote the proliferation of limbal epithelial stem cells or hair follicle stem cells. One inventive feature of the present invention lies in that the synthetic peptides are much shorter (39 amino acid residues at most) than the full-length PEDF and thus overcomes the limitations associated with the clinical use of conventional protein drugs, including high manufacturing cost, low bioavailability, and poor pharmacokinetics. Further, the present disclosure demonstrates that the synthetic peptides of this invention may be delivered transdermally, and thereby eliminates the need of an invasive delivery means (e.g., injection) as is generally required for the delivery of a protein drug. Also, findings disclosed in the present invention establish that the synthetic peptides are effective in promoting the limbal epithelial stems cells and hair follicle stem cells to proliferate, both in vivo and in vitro. Accordingly, the present synthetic peptides are useful for treating corneal and epithelial wounds.

Thus, in one aspect, the present disclosure is directed to a synthetic peptide for promoting stem cells proliferation.

According to embodiments of the present disclosure, the synthetic peptide is 20-39 amino acid residues in length, and has at least 80% amino acid sequence identity with the amino acid sequence of LSVATALSALSLGAEQRTESI-IHRALYYDLISSPDIHGT (SEQ ID NO: 1). For example, the synthetic peptide may have an amino acid sequence identity of about 80, 81, 82, 83, 84, 85, 86, 87, 88, 89, 90, 91, 92, 93, 94, 95, 96, 97, 98, 99, or 100 percent with SEQ ID NO: 1. Also, the synthetic peptide comprises at least 20 consecutive residues that are at least 90% identical to residues 11-30 of SEQ ID NO: 1. Specifically, the 20 consecutive amino acid residues may have about 90, 91, 92, 93, 94, 95, 96, 97, 98, 99, or 100 percent amino acid sequence identity with residues 11-30 of SEQ ID NO: 1.

In one embodiment, the synthetic peptide has the sequence of SEQ ID NO: 1, which is 39 amino acids in length. This synthetic peptide is also referred to as 39-mer in the examples hereinbelow. This 39-mer peptide is a short variant derived from the known 44-mer of human PEDF, which corresponds to residues 78-121 of PEDF.

Experiments provided hereinbelow confirm that there are several short, synthetic PEDF peptides derived from the 39-mer are effective in promoting the proliferation of limbal epithelial stem cells or hair follicle stem cells.

For example, a 34-mer synthetic peptide having the sequence of ALSALSLGAEQRTESIIHRALYYDLISSPDI-HGT (SEQ ID NO: 2) is proved to be effective in enhancing the HFSC and LSC proliferation according to one example provided hereinbelow. According to the process for estimating percentage of sequence identity between any two given sequences provided above, the 34-mer has a 100% amino acid sequence identity to the 39-mer, and the $6^{th}$-$25^{th}$ amino acid residues of the 34-mer has a 100% amino acid sequence identity to the amino acid residues 11-30 of the 39-mer.

Additionally, a 29-mer synthetic peptide having the sequence of SLGAEQRTESIIHRALYYDLISSPDIHGT (SEQ ID NO: 3) has been confirmed to be effective in promoting LSC and HFSC proliferations, as well as corneal and epithelial wound-healing, according to various examples hereinbelow. This 29-mer has a 100% amino acid sequence identity to the 39-mer, and the $1^{st}$-$20^{th}$ amino acid residues of the 29-mer has a 100% amino acid sequence identity to the amino acid residues 11-30 of the 39-mer.

In some examples, it is established that a 20-mer is also effective in promoting LSC and LFSC proliferations. The 20-mer has the sequence of SLGAEQRTESIIHRALYYDL (SEQ ID NO: 5), which is completely identical to the amino acid residues 11-30 of the 39-mer (100% amino acid sequence identity), and has a 100% amino acid sequence identity to the 39-mer.

Two synthetic peptides derived from mouse PEDF are also effective in promoting LSC and LFSC proliferations and corneal and epithelial wound-healing. The first mouse-derived peptide is also referred to as Mo 29-mer in the present disclosure. The Mo 29-mer has a sequence of SLGAEHRTESVIHRALYYDLITNPDIHST (SEQ ID NO: 7), which has a 83% amino acid sequence identity to 39-mer, and the first 20 amino acid residues thereof has a 90% amino acid sequence identity to the 11-30 amino acid residues of the 39-mer. Another mouse-derived peptide, Mo 20-mer has a sequence of SLGAEHRTESVIHRALYYDL (SEQ ID NO: 8). The Mo 20-mer has a 90% amino acid sequence identity to either the 39-mer or the 11-30 amino acid residues of the 39-mer.

The synthetic Peptides of the invention can be synthesized by commonly used methods such as t-BOC or FMOC protection of alpha-amino groups. Both methods involve stepwise syntheses whereby a single amino acid is added at each step starting from the C terminus of the peptide. Peptides of the invention can also be synthesized by the well-known solid phase peptide synthesis methods.

Other synthetic peptides with conservative variation with respect to the 39-mer are also contemplated. The term "conservative variation" as used herein denotes the replacement of an amino acid residue by another, biologically similar residue. Examples of conservative variations include the substitution of one hydrophobic residue such as isoleucine, valine, leucine or methionine for one another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The synthetic peptides according to above-mentioned embodiments may be formulated into compositions for promoting stem cells proliferation, which falls within another aspect of the present disclosure. In various embodiments of the present disclosure, this composition is suitable for promoting the in vivo, ex vivo, or in vitro proliferation of stem cells, in particular, LSCs and HFSCs.

According to one embodiment of the present disclosure, the composition comprises a synthetic peptide according to any of the above-mentioned aspect/embodiments, and the synthetic peptide is present in an effective amount sufficient to promote the stem cell proliferation. The composition also comprises a carrier for the synthetic peptide.

For in vitro proliferation, the carrier may be a powdered culture medium suitable for culturing the stem cells after reconstitution. The reconstitution may be achieved by first dissolving the powdered culture medium in pyrogen-free water, isotonic saline, or phosphate buffer solution; and followed by adjusting the pH of the re-constituted medium to a proper range, e.g., between 6.8 to 7.4. According to embodiments of the present disclosure, the synthetic peptide is present in the culture medium in an amount of about 1-100 nM, and preferably, about 25-50 nM. In working examples provided hereinbelow, the synthetic peptide is present at a concentration of 25 nM and 50 nM respectively in the media for culturing LSC and HFSC.

For in vivo proliferation, the carrier may be a pharmaceutically acceptable carrier suitable for administering to a living mammal, including human. For example, the pharmaceutically acceptable carrier may be any of a liquid, gel, cream, ointment, adhesive, amniotic membrane, skin substitute, artificial skin, or skin equivalents.

Some examples of substances which can serve as pharmaceutically acceptable carriers are gelatin, excipients, pyrogen-free water, isotonic saline, and phosphate buffer solutions. In one embodiment, the pharmaceutically acceptable carrier comprises an ophthalmically acceptable pharmaceutical excipient.

The choice of a pharmaceutically-acceptable carrier to be used in conjunction with a synthetic peptide is basically determined by the way the composition is to be administered. The composition of the present invention may be administered locally (e.g., topically, subconjunctivally, or intradermally) or systemically (e.g. subcutaneously).

As used herein, the term "topical administration" refers to administration onto any accessible body surface of any human or animal species, preferably the human species, for example, the skin or the outer surface of the eye. Suitable pharmaceutically-acceptable carriers for topical application include those suitable for use in liquids (including solutions and lotions), creams, gels, and the like. Advantageously, the composition is sterile and can be in dosage unit form, e.g., suitable for topical ocular use. The composition can be packaged in a form suitable for metered application, such as in container equipped with a dropper.

In one embodiment, the composition is a solution prepared using a physiological saline solution as a carrier. In another embodiment, the composition is an ointment containing the synthetic peptide at a concentration of about 50 µM. The pH of the solution or ointment is, preferably, maintained between 4.5 and 8.0 using an appropriate buffer system. A neutral pH is more preferred. Alternatively, the synthetic peptide may be incorporated in an amniotic membrane, skin substitute, artificial skin, or other skin equivalents that are suitable to be applied to the wound site.

For subconjunctival, intradermal or subcutaneous injection, the synthetic peptide may be formulated with a pharmaceutically acceptable carrier such as a sterile aqueous solution which is preferably isotonic with the blood of the recipient. Such formulations may be prepared by dissolving or suspending the solid active ingredient in water containing physiologically compatible substances such as sodium chloride, glycine, and the like, and having a buffered pH compatible with physiological conditions to produce an aqueous solution, and rendering said solution sterile.

Compositions of the invention can also comprise various additives known to those skilled in the art. For example, solvents, including relatively small amounts of alcohol, may be used to solubilize certain drug substances. Other optional pharmaceutically-acceptable additives include opacifiers, antioxidants, fragrance, colorant, gelling agents, thickening agents, stabilizers, surfactants, and the like. Other agents may also be added, such as antimicrobial agents, to prevent spoilage upon storage, i.e., to inhibit growth of microbes such as yeasts and molds. Permeation enhancers and/or irritation-mitigating additives may also be included in the composition of the present invention.

In yet another aspect, the present invention is directed to a method for promoting stem cells proliferation.

According to one embodiment, the method comprises treating the stem cells with an effective amount of the synthetic peptide according to any of the above-mentioned aspect/embodiments, thereby promoting the stem cells to proliferate. In various embodiments, the stem cells are proliferated in vivo, ex vivo, or in vitro.

In still another aspect, the present invention is directed to a method for promoting healing of a corneal or an epithelial wound in a subject. The subject may be any animal classified as a mammal, including human.

In one embodiment, the method comprises administering to the subject a therapeutically effective amount of the composition according to the above-mentioned aspect/embodiments of the present disclosure so as to promote stem cells associated with the corneal or epithelial wound of the subject to proliferate. In practice, the composition may be administered via topical administration, subconjunctival injection, subcutaneous injection, or intradermal injection.

According to some embodiments, the corneal wound is caused by pterygium; recurrent corneal erosion; limbal deficiency caused by dry eye or drug toxicity; corneal damage caused by chemical or thermal burn, or herpes virus; keratopathy induced by contact lens or radiation; corneal lesions induced by Stevens Johnson Syndrome, aniridia, limbal tumors, ocular cicatricial pemphigoid (OCP), limbal deficiency-induced corneal neovascularization, or diabetes-induced difficulty of corneal wound healing.

According to other embodiments, the epithelial wound is caused by surgical excision, skin ulcer derived from infection, chemical or thermal burn, donor site of full thickness and split thickness skin graft, bedsore, and ischemic necrosis, or diabetes-induced and age-induced difficulty of skin surface wound healing.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

Materials

HEPES-buffered Dulbecco's modified Eagle's medium (DMEM), Ham's/F12 medium, trypsin-EDTA, fetal bovine serum (FBS), antibiotic-antimycotic solutions, 0.05% trypsin-0.53 mM EDTA and anti-BrdU antibody were purchased from Invitrogen (Carlsbad, Calif.). Hydrocortisone, dimethyl sulfoxide (DMSO), insulin-transferrin-sodium selenite (ITSE) media supplement, mitomycin C (MMC), bovine serum albumin (BSA), 5-bromo-2'-deoxyuridine (BrdU), Triton X-100, Hoechst 33258 dye, formalin, and Masson's Trichrome were all from Sigma-Aldrich (St. Louis, Mo.). Dispase II and epidermal growth factor (EGF) were obtained from Roche (Indianapolis, Ind.). ΔNp63α polyclonal antibody and all the fluorescent dye-conjugated secondary antibodies were purchased from BioLegend (San Diego, Calif.). Keratin-3 (clone AE5; CBL218) was purchased from Millipore Corporation (Bedford, Mass.). Lgr6 antibody was purchased from Santa Cruz Biotechnology (sc-48236, Santa Cruz, Calif.).

Native human PEDF (SEQ ID NO: 9) was purified from human plasma via collagen I-sepharose resin as previously described by Petersen et al. (Pigment-epithelium-derived factor (PEDF) occurs at a physiologically relevant concentration in human blood: purification and characterization. Biochem J 2003; 374(Pt 1):199-206), and was analyzed by SDS/PAGE and western blotting using an anti-PEDF antibody. Short synthetic peptides (39-mer, 34-mer, 29-mer, 25-mer, 20-mer, 18-mer, Mo 29-mer, and Mo 20-mer) were synthesized and modified with acetylated at the $NH_2$ termini and amidated at the COOH termini for stability and characterized by mass spectrometry (>95% purity) to order at GenScript (Piscataway, N.J.). In addition to SEQ ID NOs: 1-3, 5, and 7-8 described hereinabove, two additional synthetic peptides were used in the examples, in which the 25-mer has a sequence of EQRTESIIHRALYYDLISSPDIHGT (SEQ ID NO: 4), whereas the 18-mer has a sequence of EQRTESIIHRALYYDLIS (SEQ ID NO: 6).

Isolation and Culture of LSCs

LSCs were isolated from six-month-old New Zealand white rabbits and used for cell-suspension culture in accordance with the method previously described by Cheng et al. (The growth-promoting effect of KGF on limbal epithelial cells is mediated by upregulation of DeltaNp63alpha through the p38 pathway. J Cell Sci 2009; 122 (Pt 24): 4473-4480) and Wang et al. (Importin 13 serves as a potential marker for corneal epithelial progenitor cells. Stem Cells 2009; 27: 2516-2526) with a slight modification. Rabbit limbal tissues were washed in PBS containing 100 U/ml penicillin and 50 μg/ml gentamicin. After carefully removing the iris, and excessive sclera, the limbal rings were exposed to dispase II (1.2 IU/ml in Hanks' balanced salt solution free of $Mg^{2+}$ and $Ca^{2+}$) at 4° C. for 16 hours. The loosened epithelial sheets were removed with a cell scraper and separated into single cells by enzymatic digestion (0.05% trypsin, and 0.01% EDTA) for 15 min at 37° C. with gentle shaking and transferred to a stop medium (9 ml of HEPES-buffered DMEM containing 10% FBS). Cells were then collected by centrifugation (400×g for 5 min).

About $1 \times 10^5$ cells were seeded on each wells of a 6-well plate and incubated in a DMEM/Ham's F-12 basal medium (10 mM HEPES, 5 ng/ml human EGF, 1% SITE liquid medium, antibiotic-antimicotic solutions, 0.5% DMSO and 0.5 μg/ml hydrocortisone) supplemented with 10% FBS for 2 days, and then shifted to a basal medium or basal medium containing 4.5 nM PEDF, 25 nM 39-mer, 25 nM 34-mer, 25 nM 29-mer, 25 nM 25-mer, 25 nM 20-mer, 25 nM 18-mer, 25 nM Mo 29-mer or 25-nM Mo 20-mer. The cells were continued cultivated at 37° C. under 5% $CO_2$ for another 3 days until they reached confluence (passage 0). LSCs were co-cultured with MMC-treated NIH-3T3 fibroblast feeder cells located within trans-well (0.4 μm pore, BD Biosciences, Bedford, Mass.). For passage purpose, near-confluent cells were harvested again by enzymatic treatment (i.e., 0.25% trypsin), and then $1 \times 10^5$ subcultured cells were further cultured in the respective medium, and proliferative capacity of cells was compared every 4 days after continuously culture-subculture (passage).

Preparation of Feeder Cells

Confluent NIH-3T3 cells were incubated with 4 μg/ml MMC for 2 hours at 37° C. under 5% $CO_2$, trypsinized and plated onto trans-well culture dishes (BD Biosciences) at a density of $2.2 \times 10^4$ cells/$cm^2$. These feeder cells were used 4 to 24 hours after plating.

Immunofluorescence Analysis

De-paraffinized tissue sections or 4% paraformaldehyde-fixed LSCs were blocked with 10% goat serum and 5% BSA in PBST (PBS containing 0.1% Tween-20) for 1 hour. Staining was done using primary antibodies against ΔNp63α (1:150 dilution), BrdU (1:250 dilution), and keratin-3 (1:250 dilution) at 37° C. for 2 hours, followed by incubation with the appropriate rhodamine- or FITC-conjugated donkey IgG (1:500 dilution) for 1 hour at RT. Nuclei were identified by counterstaining with Hoechst 33258 for 7 minutes. Images were captured using a Zeiss epifluorescence microscope with a CCD camera and photographs were taken by using the Axiovert software.

BrdU Labeling $2 \times 10^5$ limbal cells (the $1^{st}$ passage) were seeded at a slide coated with FNC COATING MIX® solution (Athena Enzyme Systems, Baltimore, Md.) and incubated with a culture medium for one day. BrdU (final, 10 μM) was added to the culture for 2 hours. After being fixed with 4% paraformaldehyde, cells were exposed to cold methanol for 2 minutes, and then treated with 1 N HCl at RT for 1 hour before performing immunofluorescence. For animal study, BrdU was reconstituted in DMSO as stock (80 mM). 10 μl of BrdU mixed with 90 μl of PBS was intraperitoneally injected into mouse 3 hours prior to euthanasia. DNA synthesis was assessed by BrdU labeling with anti-BrdU antibodies.

Corneal Wounding and Treatments

The experiments were performed using eight-week-old female C57BL/6 mice, and the procedures were approved by the Mackay Memorial Hospital Review Board for animal investigation. Animals were anesthetized by an intraperitoneal injection of a mixture of zoletil (6 mg/kg) and xylazine (3 mg/kg). One filter paper (0.9 mm diameter) soaked with 20% ethanol was placed on the central cornea of right eye for one minute and then irrigated extensively with PBS. Subsequently, mechanical epithelial scrape was performed using a punch under a dissection microscope to create a circular injury (2 mm diameter) at the entire corneal region of the mouse eye without encroaching the corneal stroma, limbus or conjunctiva.

Each synthetic peptide (the 39-mer, 34-mer, 29-mer, 25-mer, 20-mer, 18-mer, Mo 29-mer or Mo 20-mer) was reconstituted in DMSO as stock (5 mM) and mixed with TOBREX® eye ointment (Alcon; containing 0.3% Tobramycin and 0.5% Chlorobutanol) to a concentration 50 μM. In each of the treatment group (n=6-10), the right eye was treated with 20 μl eye ointment containing the synthetic peptide once a day after the scrape injury. In the control group (n=20), right eye was treated with 20 μl of eye ointment mixed with vehicle DMSO. Wound size was determined by staining with topical fluorescein (Fluor-I-Strip, Ayerst Laboratories, Philadelphia, Pa.) and photographed with a digital camera. The area of defect was quantified from the photographs using a computer-assisted image analyzer (Adobe Photoshop CS3 10.0) and was calculated as the percentage of residual epithelial defect at each time point/initial wound area.

Cultivation of Hair Follicle Stem Cells

Human hair follicles were collected from hairs of healthy donors. The follicles were dissected with tweezers under microscope and most of adipose and connective tissue was removed. The bulge region of hair follicle under the sebaceous gland was cut and then bulge fragments (including central isthmus) were transferred into a 35-mm dish containing 1 ml of collagenase A (1 mg/ml; Roche) and incubated for 1.5 hours at 37° C. to digest the collagen capsule. Subsequently, the bulge fragments were transferred into a fresh cell culture dish containing dispase II (2.4 U/ml)/0.05% trypsin and further incubated for 1.5 hours at 37° C. to obtain a single cell suspension.

After mechanical dissection and enzymatic digestion, the suspended bulge cells isolated from five bulge fragments were seeded into a well of 12-well culture plate and incubated with the basal medium for 5 days to facilitate cell adhesion. The basal medium contains four parts Gibco calcium-free Dulbecco's modified Eagle's medium (DMEM) and one part Ham's F12 medium (calcium concentration reached about 0.25 mM) and supplemented with 10% FBS, 10 ng/ml human epidermal growth factor, 500 mg/I L-glutamine, 0.2% bovine pituitary extract, 0.18 g/ml hydrocortisone, 1% ITSE as well as antibiotic-antimicotic solutions. Cultivation method was similar to that of Blazejewska et al. (Stem Cells 2009; 27:642). After 5 days of incubation, cells were cultured in the serum-free basal medium or basal medium containing 4.5 nM PEDF, 50 nM 29-mer, or 50 nM 20-mer, until near confluence (about 2 weeks; passage 0). The medium was changed every 2 to 3 days. The bulge cells were co-cultured with 3T3 fibroblast feeder cells. For passage, near-confluent cells were harvested by enzymatic treatment (i.e., 0.25% trypsin) for 5 min at 37° C. Approximately $1 \times 10^5$ human bulge cells were transferred to a new dish and allowed to grow for 14 days to near confluence (passage 1).

Skin Wound Healing

To perform full-thickness skin excision, 8- to 10-week-old C57L/B6 mice were respectively anesthetized by an intraperitoneal injection of a mixture of zoletil (6 mg/kg) and xylazine (3 mg/kg). Two full-thickness skin excisional wounds, 4 mm in diameter were made on either side of the dorsal midline using Sklar Tru-Punch disposable biopsy punch (Sklar, West Chester, Pa., USA). In each treatment group (n=6), the skin wound was treated with 25 µl skin ointment (containing 50 µM synthetic peptide and 0.006 µl DMSO vehicle) once daily after the skin scraping. In the control group (n=6), skin wound was treated with 25 µl of skin ointment with equal concentration of DMSO. Each gram of the above skin ointment contains 5 mg neomycin sulfate and 12.5 mg Bacitracin Zinc. Wounds were left uncovered and harvested 4 and 7 days after injury. Mice were housed individually during the healing period.

The area of wound was quantified from the photographs using a computer-assisted image analyzer (Adobe Photoshop CS3 10.0) and was calculated as the percentage of residual epithelial defect at each time point/initial wound area.

For histological analysis the complete wounds including 2 mm of the epithelial margins was isolated, bisected, fixed overnight in 4% PFA in PBS, and embedded in paraffin. Sections (5 µm) from the middle of the wound were stained using the Masson's trichrome procedure as described by the manufacturer, in which the epithelium was stained red and connective tissue was stained blue. Photographs were taken using a Leica DC 500 camera (Leica Microsystems).

Statistics

Results were expressed as the mean±standard error of the mean (SEM). 1-way ANOVA was used for statistical comparisons. $P<0.05$ was considered significant, unless otherwise specified.

Example I

PEDF-Derived Short Synthetic Peptides Promote In Vitro LSC Proliferation

To identify the functional domain responsible for activating LSC proliferation, surface probability and hydrophilicity of the PEDF protein (123 amino acids from positions 78-200 of the 418 amino acids of human PEDF; GenBank number U29953) were analyzed and the amino acid sequence from positions 83-121 (referred as 39-mer) was identified to be the most variable region. A serial of short peptides respectively cover amino acid sequence from residues 83-121 of PEDF, and variants thereof were synthesized and then used to investigate their respective efficacy on proliferating LSCs in culture.

To determine the effects of PEDF-derived short peptides may have on the self-renewal of LSCs, LSC proliferation was examined by BrdU pulse-labeling (2 hours; red color) and LSC phenotype was revealed by immunostaining ΔNp63α (green color).

Figure 1B:
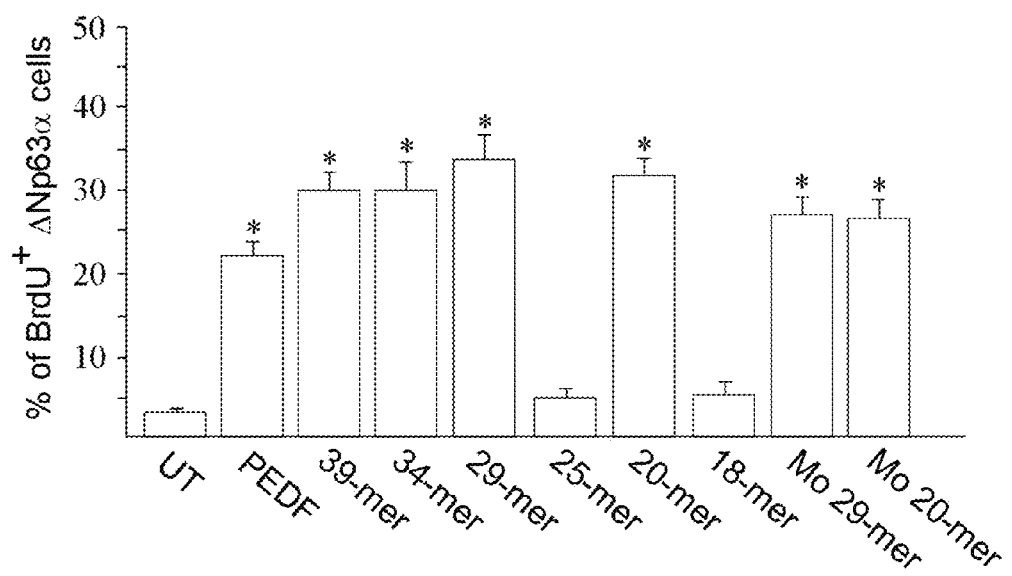

As demonstrated in FIG. 1A, proliferation of LSCs cultivated in medium containing full-length PEDF, 39-mer, 34-mer, 29-mer, or 20-mer was more significant than that in control medium (FIG. 1B; 22.0±1.5%, 30.1±1.9%, 30.0±3.4%, 33.9±2.6% and 31.8±1.7% versus 3.0±0.5%). By contrast, enhanced proliferation was not observed in LSCs cultivated in a medium containing the synthetic 25-mer and 18-mer PEDF.

Mo 29-mer and Mo 20-mer are derived from mouse PEDF, and they differ from human 29-mer and human 20-mer by 4 and 2 amino acid residues, respectively. These mouse PEDF-derived short peptides displayed the mitogenic activity to LSCs with an extent similar to their human counterparts (FIG. 1B; 27.1±1.8% and 26.3±2.2%). Collectively, LSC expansion in culture may be enhanced by medium supplemented with the full-length PEDF, 39-mer, 34-mer, 29-mer, 20-mer, Mo 29-mer, or Mo20-mer.

Example II

PEDF-Derived Short Synthetic Peptides Promote In Vivo Corneal Wound-Healing

Figure 2A:
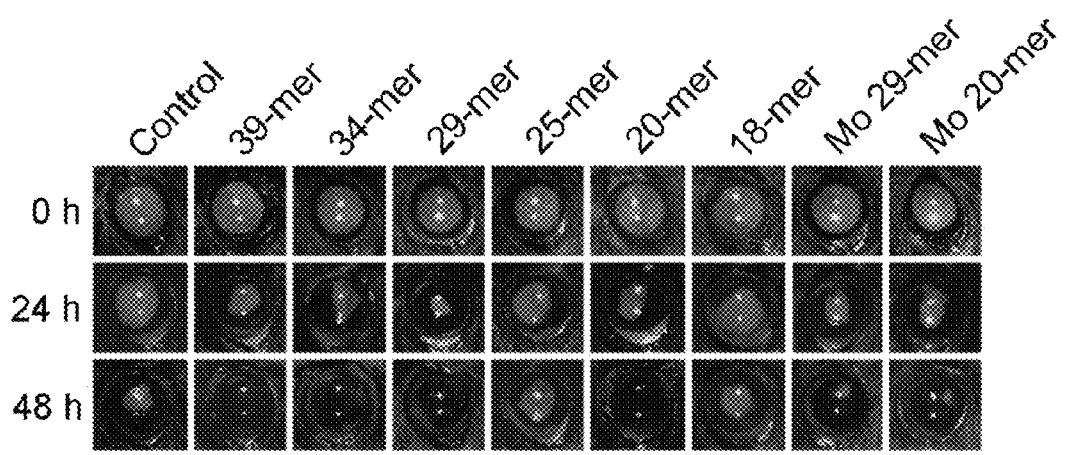
FIG. 2A provides photographs and FIG. 2B is a histogram, and together, they illustrate the corneal wound-healing of mice from treatment groups according to another example of the present disclosure. Mice eyes were stained with topical fluorescein after formation of a 2 mm corneal wound followed for 48 hours and then photographs of the fluorescein-stained corneas were captured with a CCD camera (Olympus). Nine groups of mice were included: controls receiving 20 µl of eye ointment mixed with DMSO (less than 0.05 µL) and mice given 20 µl of a short peptide (50 µM)-mixed eye ointment once a day. Wound area was measured by Adobe Photoshop CS3 10.0. Histogram of residual epithelial defect (%) in mice corneas is presented as percentage of the original wound. Significantly different from control groups at 24 hours and 48 hours. *$P<0.05$ versus control group.
Figure 2B:
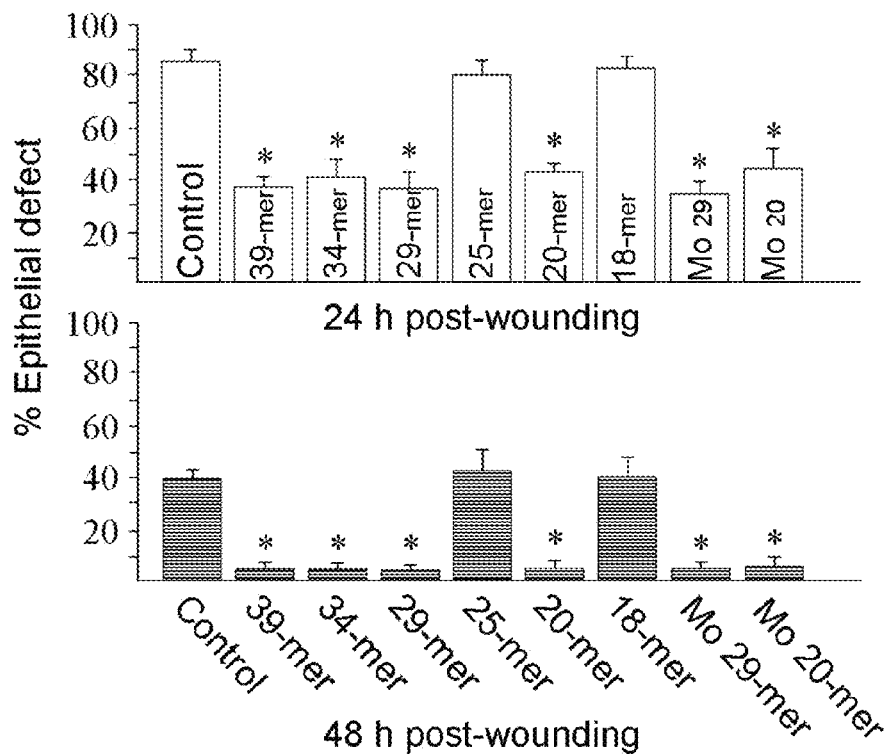

To investigate the effect of PEDF-derived short peptides on corneal wound healing in mice, corneal wound was created by a circular punch (2 mm diameter), then control eye-ointment or eye-ointment containing the short synthetic PEDF peptide(s) of this invention was applied to the wounded eye, and wound healing was subsequently evaluated by fluorescein staining. No significant differences in the size of the initial abrasion were noted between synthetic PEDF peptide-treated and control mice. After 48 hours, complete corneal re-epithelialization was found in mice treated with either 39-mer, 34-mer, 29-mer, 20-mer, Mo 29-mer, or Mo 20-mer, whereas control group mice and mice treated with 25-mer or 18-mer exhibited incompletely healed wounds (FIG. 2A). 39-mer, 34-mer, 29-mer, 20-mer, Mo 29-mer, or Mo 20-mer treatment resulted in significantly smaller epithelial defect than that of the control mice at 24 hours (37.2±4.3%, 40.6±7.2%, 36.5±6.4%, 42.2±4.3%, 33.8±5.2% and 43.9±7.6% versus 84.9±5.1%) and 48 hours (4.8±2.7%, 4.6±2.1%, 3.7±2.9%, 5.0±3.7%, 4.6±2.3%, and 6.2±3.5% versus 39.5±3.1%) (FIG. 2B).

Example III

Figure 3A:
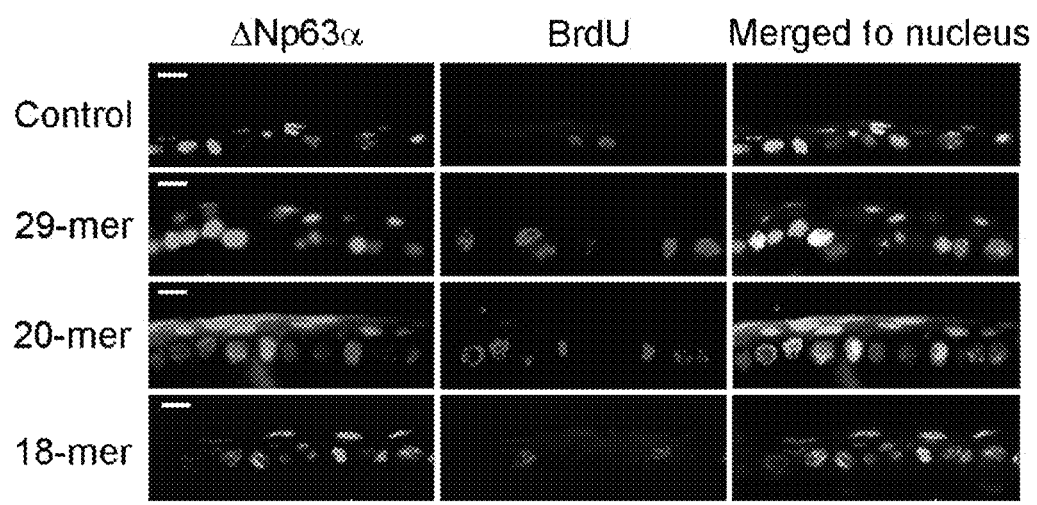
FIG. 3A provides immunofluorescence microscopy photographs and FIG. 3B is a histogram, and together, they illustrate the in vivo limbus proliferation at 24 hours post-corneal injury according to the previous example of the present disclosure. Double immunofluorescence of sections of control ointment and PEDF-derived short peptides (29-mer, 20-mer and 18-mer) ointment-treated eyes stained with BrdU- and $\Delta$Np63$\alpha$-specific antibodies. $\Delta$Np63$\alpha$ is expressed in the cell nucleus as confirmed by Hoechst 33258 counterstaining. $P<0.005$ versus control eye.
Figure 3B:
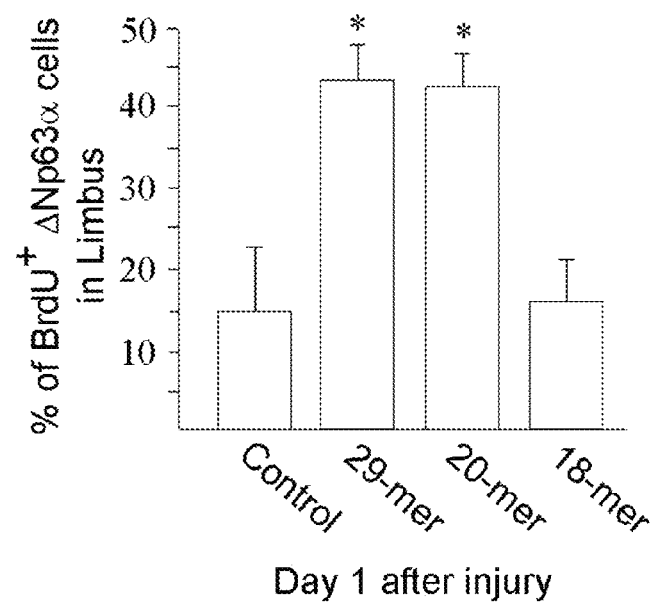

PEDF-Derived Short Synthetic Peptides Promotes In Vivo LSC Proliferation after Corneal Wounded To investigate whether the LSC proliferation during corneal wound healing could be accelerated by the synthetic peptide of this invention, mice were intraperitoneally received BrdU and euthanized at 24 hours after corneal wounding. ΔNp63α (green) and BrdU (red) double-immunostaining of ocular sections revealed that the levels of BrdU- and ΔNp63α-positive cells in the limbus of 29-mer and 20-mer treated eyes were elevated, as compared with that of the control eyes (FIGS. 3A and 3B; 43.2±4.6% and 42.4±4.3% versus 15.0±7.6%); whereas the level of LSC proliferation in 18-mer treated eyes was similar to that of the control animals.

Figure 4A:
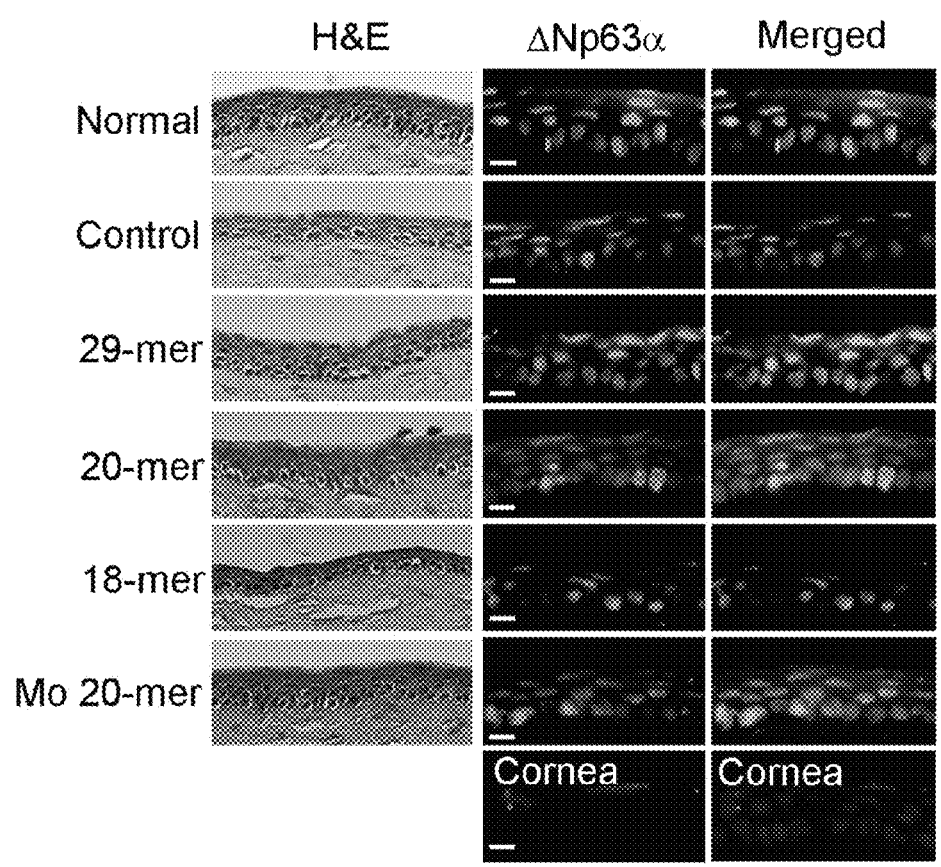
FIG. 4A provides histologic photographs (left panels, Hematoxylin and Eosin (H&E) staining, magnification, ×400), immunofluorescence microscopy photographs (middle panels, magnification, ×1000), and merged photographs (right panels); together, they illustrate layers of stratified limbal epithelium of mice at day 5 post-corneal injury according to the previous example of the present disclosure. Immunofluorescence analysis showed the distribution and level of $\Delta$Np63$\alpha$-positive cells at limbus. Normal indicates uninjured eye. Cornea of normal eye that has no $\Delta$Np63$\alpha$-positive cell acted as $\Delta$Np63$\alpha$ negative immunostaining control.
Figure 4B:
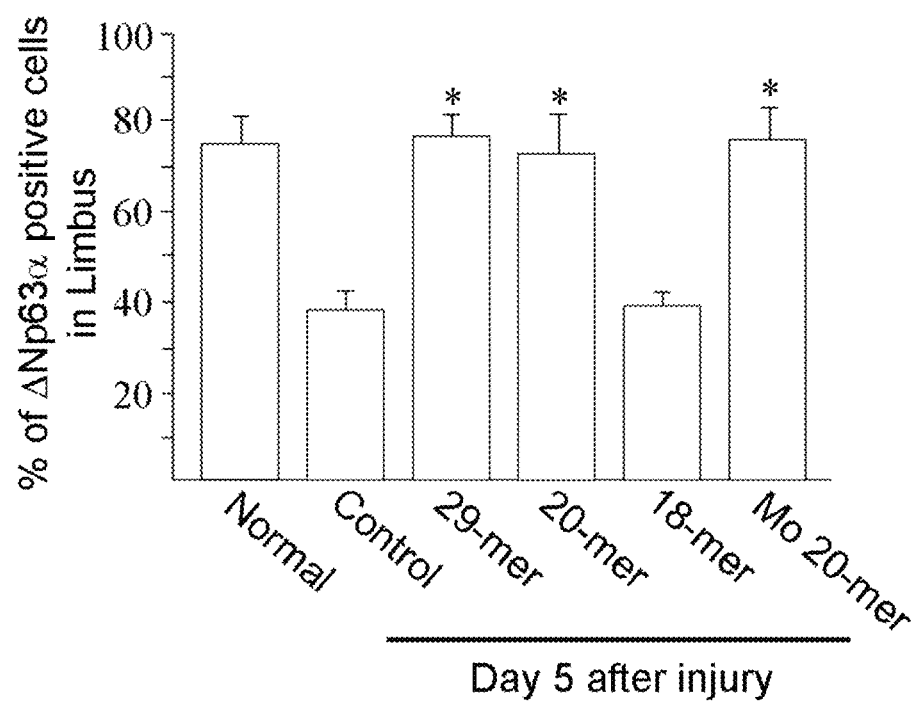
FIG. 4B is a histogram illustrating levels of $\Delta$Np63$\alpha$-positive cells at limbus. Results of immunofluorescence were evaluated from 6 sections per mouse cornea, and 6 mice at each treatment. A labeling index was computed as the number of labeled cells divided by the total number of cells observed by a Hoechst 33258 fluorescent nuclear stain. $P<0.005$ versus control eye.

On day 5 post-wounding, HE stain and ΔNp63α (green) immunostaining of ocular sections revealed that the thickness of the limbus of 29-mer, 20-mer and Mo 20-mer-treated eyes returned to full-thickness of stratified layers, as compared with that of the normal unwounded eye; whereas the limbal epithelia of 18-mer treated- or control ointment-treated eyes were thinner, and with fewer ΔNp63α-positive LSCs present (FIG. 4A). On average, the levels of ΔNp63α-positive LSCs in limbus of normal unwounded eye is 74.8±6.3%; whereas the levels of ΔNp63α-positive LSCs in corneal wounded eyes treated with control, 29-mer, 20-mer, 18-mer and Mo 20-mer ointment were 38.9±2.8%, 77.0±4.1%, 73.1±8.6%, 39.4±2.6%, and 76.3±6.2% respectively (FIG. 4B). Taken together, 29-mer or 20-mer treatment can activate LSCs in vivo coincidently with more prominent corneal re-epithelialization than corneal regeneration by native progress.

The results from the preceding examples establish that present synthetic PEDF peptides (such as the 29-mer, 20-mer, Mo 29-mer, and Mo 20-mer) may enhance proliferation while suppresses spontaneous differentiation of LSCs in cultures. This may significantly improve the quality of limbal equivalent and is therefore advantageous to the corneal regenerative medicine. The direct stimulation of the proliferation of limbal progenitor cells and the ensued acceleration of corneal re-epithelialization suggest that the present synthetic PEDF peptides may act as potential agents to treat LSC deficiency-related disorders.

Example IV

PEDF-Derived Short Synthetic Peptides Promote In Vitro Proliferation of HFSCs

Figure 5A:
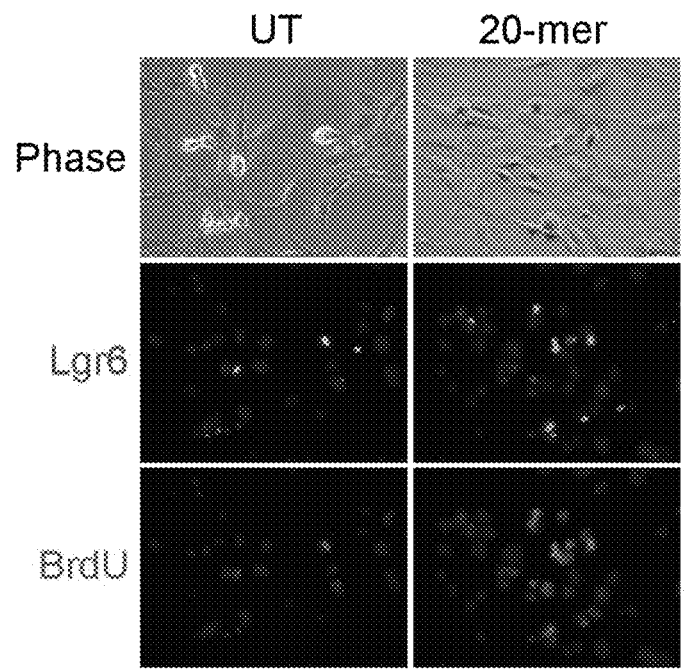
FIG. 5A provides immunofluorescence microscopy photographs and FIG. 5B is a histogram, and together, they illustrate the in vitro proliferation of HFSCs from treatment groups according to one example of the present disclosure. HFSC proliferation was determined by BrdU labeling for 2 hours. HFSCs (Lgr6, green) and BrdU (red) were detected by immunofluorescence microscopy (original magnification, ×1000). Twenty randomly selected fields in each group were photographed, and the percentage of BrdU and Lgr6-double positive cells (pale pink) per total Lgr6-positive cells was calculated. *P<0.001 versus untreated cells.
Figure 5B:
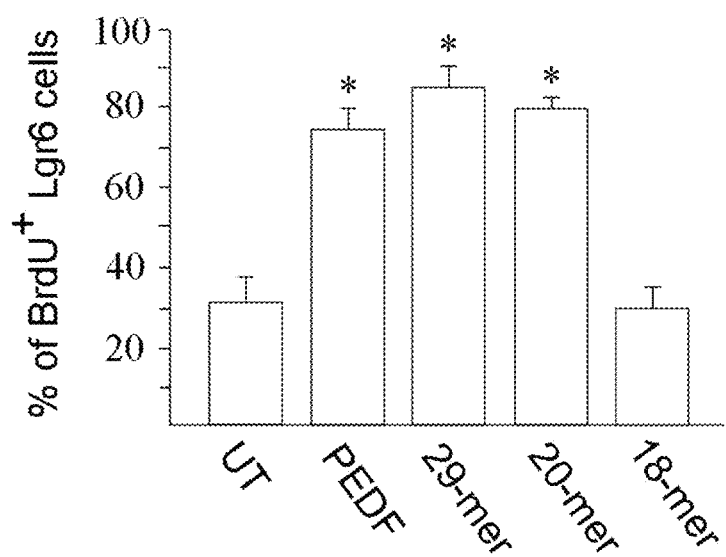

The effects of full-length PEDF and its short peptides on the HFSC proliferation was investigated in this Example using BrdU pulse-labeling (2 hours; red color), and HFSC phenotype was revealed by immunostaining Lgr6 (green color). As demonstrated in FIG. 5A, proliferation of human HFSC cultivated in medium containing 20-mer was more significant than those cultivated in control medium. FIG. 5B illustrated that for the groups treated with full-length PEDF, 29-mer and 20-mer, the percentage of BrdU and Lgr6-double positive cells per total Lgr6-positive cells is 73.8±6.0%, 86.2±3.9% and 79.5±2.6%, in contrast to 31.9±5.6% and 30.1±6.3% of the control and 18-mer-treated groups.

Example V

PEDF-Derived Short Synthetic Peptides Accelerate Epithelial Wound-Healing

Figure 6A:
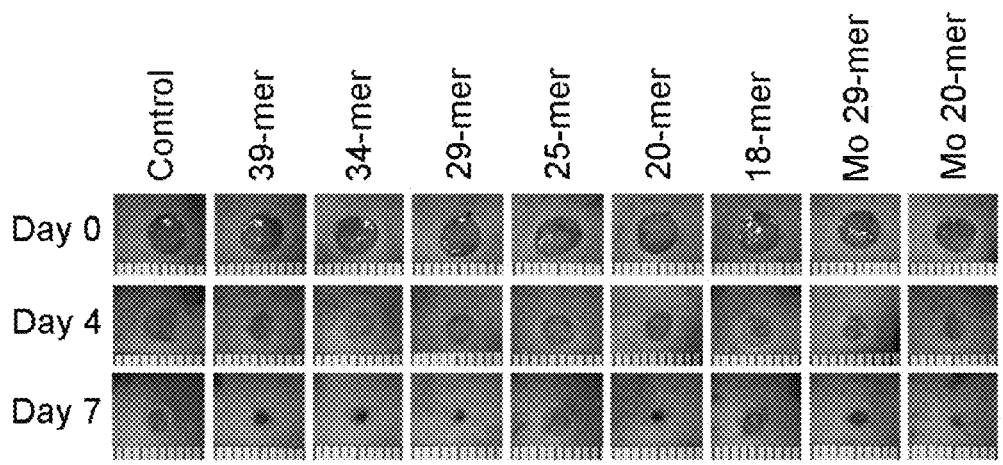
FIG. 6A provides photographs and FIG. 6B is a histogram, and together, they illustrate the skin (epithelial) wound-healing of mice from treatment groups according to another example of the present disclosure. 4 mm punch wounds were made on the dorsal side of C57/B6 mice. Skin ointment was treated once a day. Photographs of the wounded skin and ruler (scale 10 mm) were captured with a CCD camera (Olympus). The residual epithelial defect (%) is presented as percentage of the original wound. Data are shown as mean±SE. Significantly different from control groups are post-wounding for 4 and 7 days (*P<0.05).
Figure 6B:
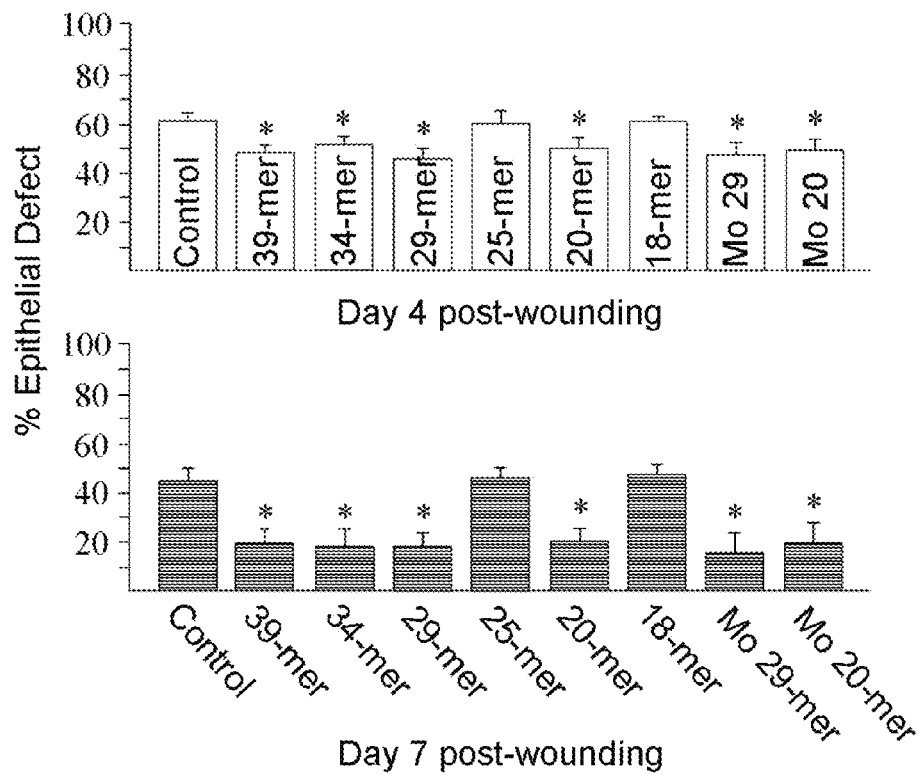

Referring to FIG. 6A, groups treated with 39-mer, 34-mer, 29-mer, 20-mer, Mo 29-mer and Mo 20-mer showed enhanced wound healing on day 4, post-injury. The residual epithelial defects of these groups on day 4 were 48.1±3.2%, 41.4±2.5%, 46.3±3.7%, 50.1±3.8%, 47.8±4.3%, and 49.6±3.9%, respectively; as compared to 61.5±3.2% of the control group (FIG. 6B). At day 7 post-injury, the wounds in animals treated with these peptides respectively exhibited near complete healed wounds, and scars were less observed (FIG. 6A). The residual epithelial defects in these groups at day 7 were 18.4±5.7%, 17.9±6.1%, 18.2±4.3%, 20.0±4.9%, 16.8±6.6% and 20.3±7.5%, respectively; as compared to the control group of 44.5±5.3% (FIG. 6B). However, 25-mer and 18-mer were not able to promote wound healing (FIGS. 6A and 6B). The results indicated that PEDF-derived short peptides according to the present disclosure (e.g., 39-mer, 34-mer, 29-mer, 20-mer, Mo 29-mer, and Mo 20-mer) benefit skin re-epithelialization.

Figure 7A:
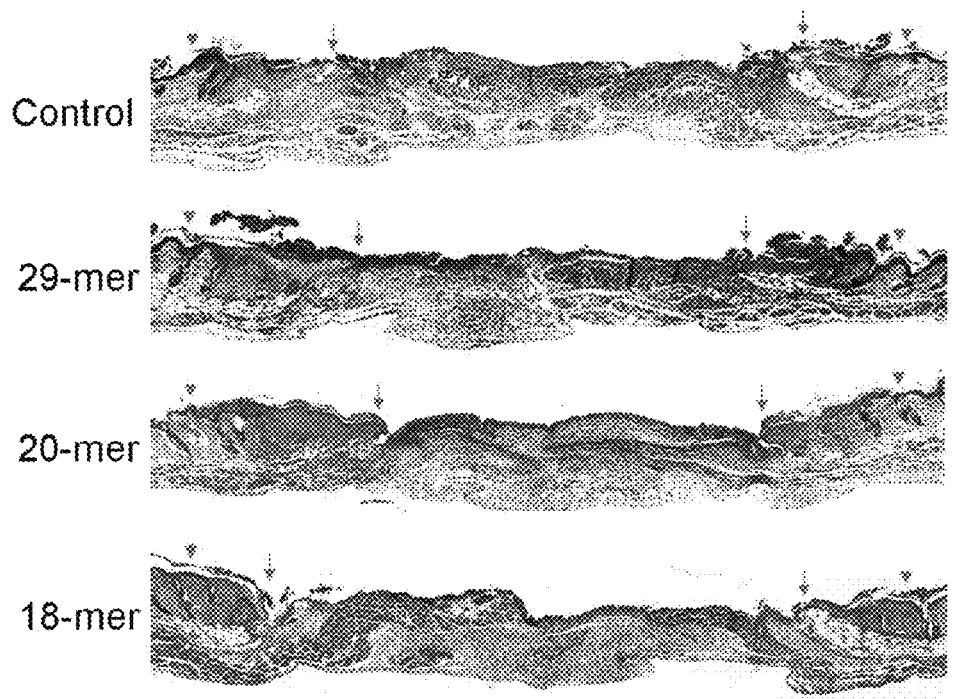
Figure 7B:
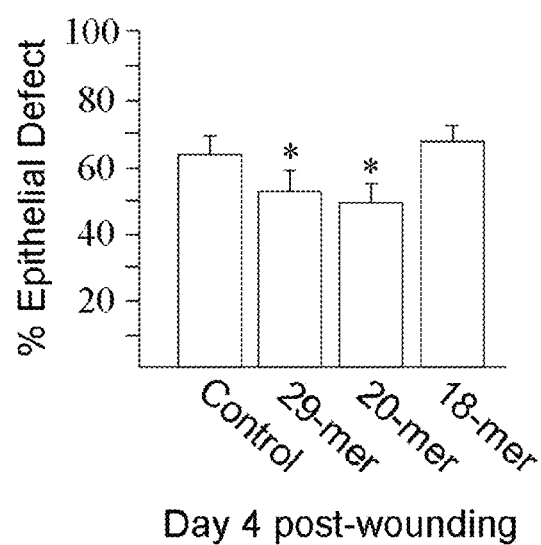

To further confirm the efficacy of 29-mer and 20-mer on skin wound repair, skin sections from day 4 after trauma were stained using the Masson's trichrome. Referring to FIG. 7A, it is evident that animals treated with 29-mer and 20-mer exhibited better wound healing than control group. The residual epithelial defect of 29-mer and 20-mer-treated groups were 52.7±6.2% and 49.7±5.6%, respectively; as compared to control animals of 63.8±5.8% (FIG. 7B). In addition, 29-mer treatment elevated the thicknesses of hyper-proliferative epithelial (HE) tissue and granulation tissue (GT) around the edge of the wound (FIG. 7C). Quantitative results of the area of HE tissue indicated that the skin thickness in 29-mer and 20-mer treated groups were 1.41±0.25 and 1.32±0.21 folds over that of the control group, respectively (FIG. 7D). In addition, quantitative results of the area of GT indicated that the skin thickness in 29-mer and 20-mer treated animals were respectively 1.45±0.23 and 1.37±0.17 folds more than those of the control group (FIG. 7E).

Figure 8A:
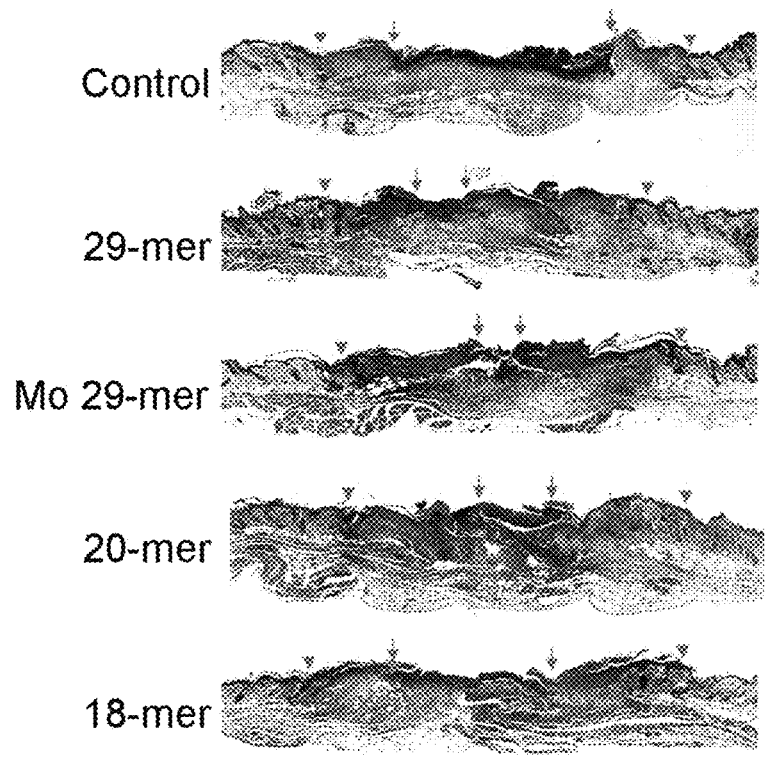
FIGS. 8A and 8B provide quantification of wound healing at day 7.
Figure 8B:
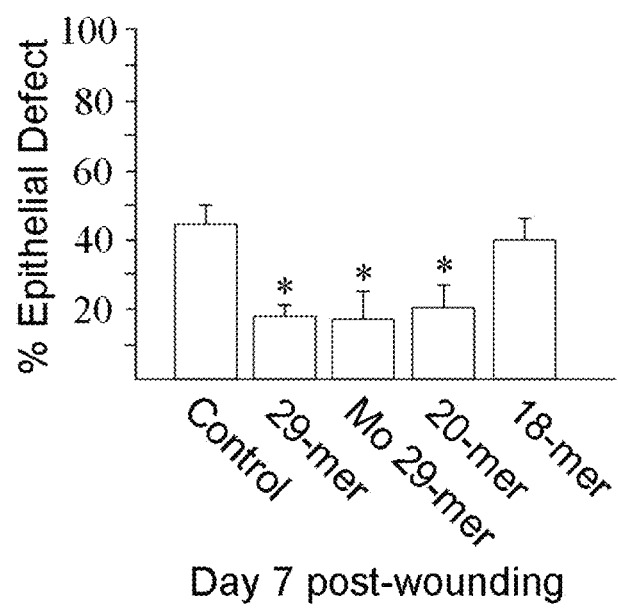

Masson's trichrome was used to stain skin sections obtained from day 7 after trauma for the measurement of the wound closure. 29-mer, Mo 29-mer, or 20-mer-treated wounds exhibited better re-epithelialization, in which the smaller residual epithelial defects was identified than that of the control ointment-treated wound (FIGS. 8A and 8B; 17.9±3.3%, 17.2±7.3%, and 20.8±6.1% versus 43.5±6.5%).

Example VI

PEDF-Derived Short Synthetic Peptides Accelerate Epithelial Wound-Healing by Promoting Proliferation in the Basal Cells of the Hyper-Proliferative Epithelium To investigate whether skin resurfacing process, which involves cell replication, is accelerated by 29-mer, Mo 29-mer, 20-mer, or Mo 20-mer, wounds were treated with skin ointment containing 29-mer, Mo 29-mer, 20-mer, or Mo 20-mer for 4 days, and then mice were intraperitoneally injected with BrdU for further 3 hours before euthanized.

Figure 9A:
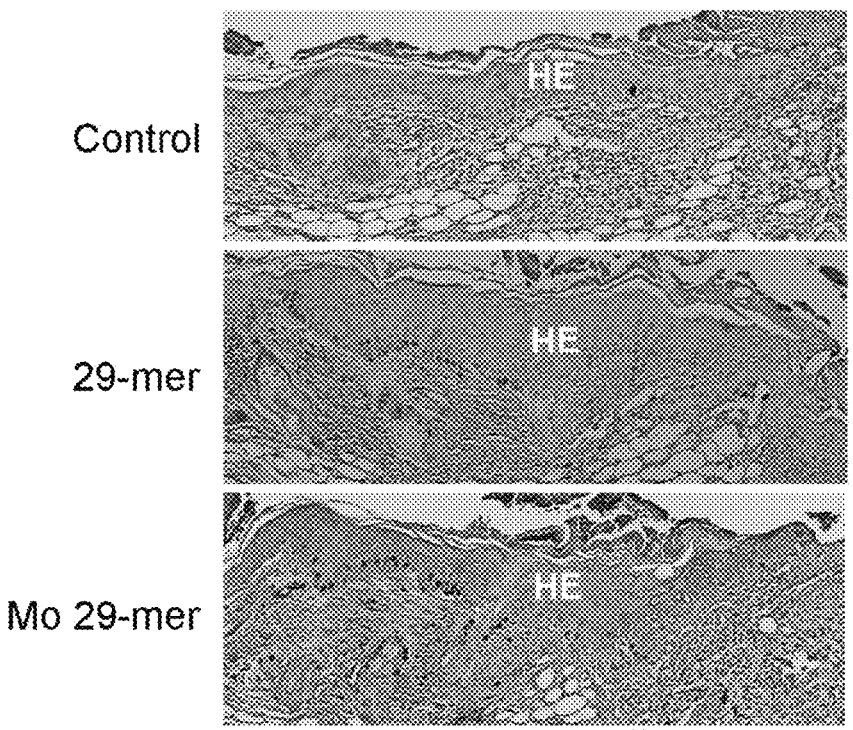
FIGS. 9A and 9B illustrate histological analysis of cell replication at day 4 post-skin wounding.
Figure 9B:
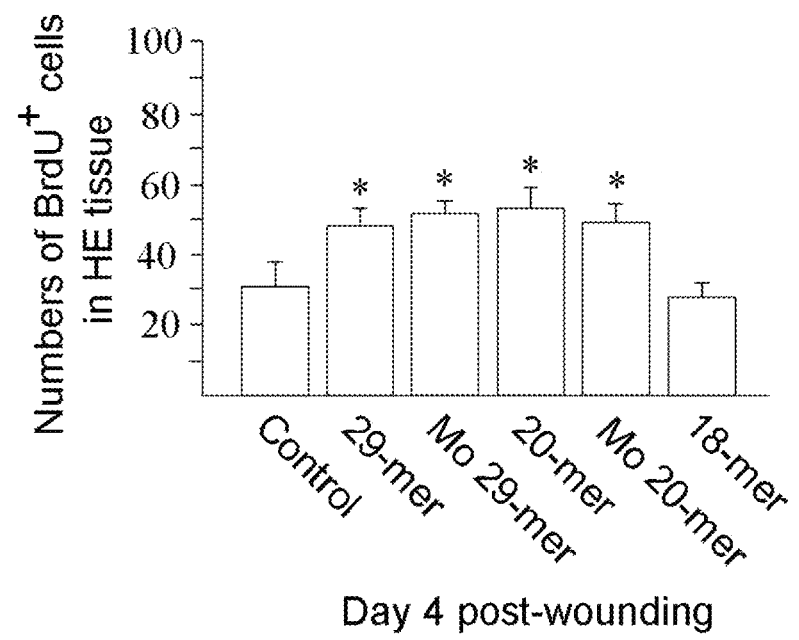

Immunohistochemical analysis of skin specimens using the anti-BrdU antibody revealed that the distributions of BrdU-positive cells are principally located at the basal layer of HE tissue and the bulge region of hair follicle (FIG. 9A). The numbers of BrdU-positive cells in 29-mer, Mo 29-mer, 20-mer, and Mo 20-mer-treated wounds increased significantly; as compared with that of the control wound (FIG. 9B; 47.9±5.0%, 52.5±2.5%, 53.1±6.5% and 49.2±4.3% versus 30.8±8.1%). This observation was consistent with the thicker HE tissue treated with 29-mer or 20-mer.

Example VII

Figure 10A:
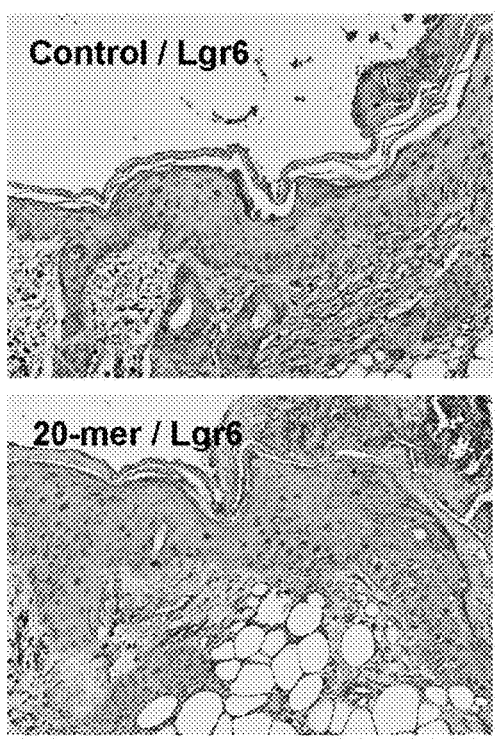
FIGS. 10A and 10B illustrate histological analysis of the distribution of HFSCs at day 4 post-skin wounding.
Figure 10B:
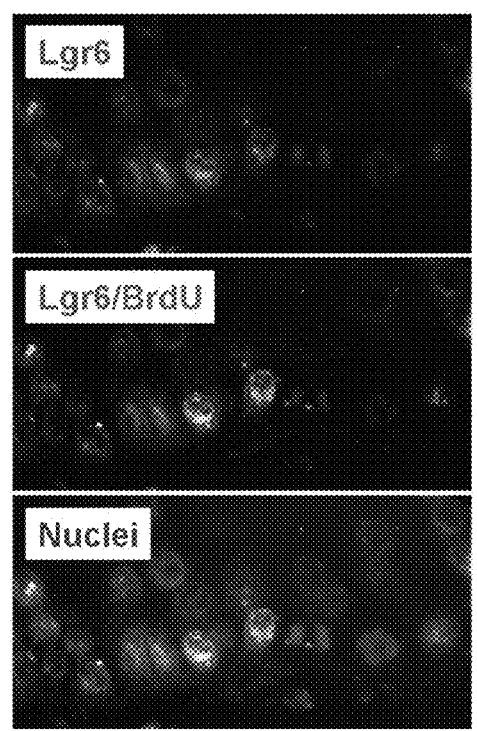

PEDF-Derived Short Synthetic Peptides Promotes HFSC Proliferation after Skin being Wounded Lgr6-positive HFSCs is an important precursor cells for epithelium repair during skin wound healing. As demonstrated in FIG. 10A, immunohistochemical analysis of skin specimens obtained from wounds treated with 20-mer for 4 days revealed that the Lgr6-positive cells were markedly increased at HE tissue, as compared with that of the control wound. Immunohistochemical studies also revealed that Lgr6-positive cells were partly located at the basal layer of HE tissue. This observation is consistent with the finding that cell proliferation mainly occurred at basal layer of HE tissue. Dual-immunostaining further confirmed that Lgr6-positive basal cells (green) are responsible for the enhanced proliferation found in HE tissue induced by the synthetic 20-mer (FIG. 10B).

The results from the preceding examples establish that present synthetic PEDF peptides (such as the 20-mer, 29-mer, 34-mer, 39-mer, Mo 20-mer, and Mo 29-mer) may enhance proliferation of HFSCs in cultures. Specifically, the enhanced proliferation of HFSCs is associated with re-epithelialization and wound-healing. Accordingly, the present synthetic PEDF peptides are suitable for use as a therapeutic agent to promote wound-healing, especially for healing wounds with large area or wounds that are difficult to heal due to diabetes or aging.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A synthetic peptide for promoting the proliferation of limbal epithelial stem cells or hair follicle stem cells, wherein,
the amino acid sequence of the synthetic peptide consists of 20-39 amino acid residues in length and has at least 80% amino acid sequence identity to SEQ. ID NO: 1;
the N-terminus of the amino acid sequence is acetylated and the C-terminus of the amino acid sequence is amidated; and
at least 20 consecutive residues of the synthetic peptide has at least 90% amino add sequence identity to residues 11-30 of SEQ ID NO: 1 and comprises four consecutive residues identical to residues 11-14 (SLGA) of SEQ ID NO: 1.

2. The synthetic peptide of claim 1, wherein the amino acid sequence is selected from the group consisting of SEQ ID NO: 1, SEQ ID NO: 2, SEQ ID NO: 3, and SEQ ID NO: 5.

3. A composition for promoting the proliferation of limbal epithelial stem cells or hair follicle stem cells, comprising,
an effective amount of the synthetic peptide of claim 1, and
a carrier.

4. The composition of claim 3, wherein the carrier is a powdered culture medium suitable for culturing the stem cells.

5. The composition of claim 4, wherein the synthetic peptide is present in an amount of 1-100 nM.

6. The composition of claim 5, wherein the synthetic peptide is present in an amount of 25-50 nM.

7. The composition of claim 3, wherein the carrier is a pharmaceutically acceptable carrier selected from the group consisting of a liquid, gel, cream, ointment, adhesive, amniotic membrane, skin substitute, artificial skin, and skin equivalents.

8. The composition of claim 3, wherein the amino acid sequence is selected from the group consisting of SEQ ID NO: 1, SEQ ID NO: 2, SEQ ID NO: 3, and SEQ ID NO: 5.

9. A composition for promoting the proliferation of limbal epithelial stem cells or hair follicle stem cells, comprising,
an effective amount of a synthetic peptide, wherein the amino acid sequence of the synthetic peptide consists of 20-39 amino acid residues in length and has at least 80% amino acid sequence identity to SEQ ID NO: 1, and at least 20 consecutive residues of the synthetic peptide has at least 90% amino acid sequence identity to residues 11-30 of SEQ ID NO: 1 and comprises four consecutive residues identical to residues 11-14 (SLGA) of SEQ ID NO: 1; and
a pharmaceutically acceptable carrier selected from the group consisting of a gel, cream, and ointment.

10. The composition of claim 9, wherein the amino acid sequence is selected from the group consisting of SEQ ID NO: 1, SEQ ID NO: 2, SEQ ID NO: 3, and SEQ ID NO: 5.

11. The composition of claim 9, further comprising an antibiotic and/or antimycotic agent.

12. A composition for promoting skin or corneal wound healing, comprising,
an effective amount of a synthetic peptide consisting of an amino acid sequence that is 20-39 amino acid residues in length and has at least 80% amino acid sequence identity to SEQ ID NO: 1, and at least 20 consecutive residues of the synthetic peptide has at least 90% amino acid sequence identity to residues 11-30 of SEQ ID NO: 1 and comprises four consecutive residues identical to residues 11-14 (SLGA) of SEQ ID NO: 1;
an antibiotic and/or antimycotic agent; and
a pharmaceutically acceptable carrier.

13. The composition of claim 12, wherein the carrier is a pharmaceutically acceptable carrier selected from the group consisting of a liquid, gel, cream, ointment, adhesive, amniotic membrane, skin substitute, artificial skin, and skin equivalents.

14. The composition of claim 12, wherein the amino acid sequence is selected from the group consisting of SEQ ID NO: 1, SEQ ID NO: 2, SEQ ID NO: 3, and SEQ ID NO: 5.

* * * * *

SEQUENCE LISTING

```
<160> NUMBER OF SEQ ID NOS: 9

<210> SEQ ID NO 1
<211> LENGTH: 39
<212> TYPE: PRT
<213> ORGANISM: Artificial Sequence
<220> FEATURE:
<223> OTHER INFORMATION: synthetic peptide

<400> SEQUENCE: 1

Leu Ser Val Ala Thr Ala Leu Ser Ala Leu Ser Leu Gly Ala Glu Gln
1               5                   10                  15

Arg Thr Glu Ser Ile Ile His Arg Ala Leu Tyr Tyr Asp Leu Ile Ser
            20                  25                  30

Ser Pro Asp Ile His Gly Thr
        35

<210> SEQ ID NO 2
<211> LENGTH: 34
<212> TYPE: PRT
<213> ORGANISM: Artificial Sequence
<220> FEATURE:
<223> OTHER INFORMATION: synthetic peptide

<400> SEQUENCE: 2

Ala Leu Ser Ala Leu Ser Leu Gly Ala Glu Gln Arg Thr Glu Ser Ile
1               5                   10                  15

Ile His Arg Ala Leu Tyr Tyr Asp Leu Ile Ser Ser Pro Asp Ile His
            20                  25                  30

Gly Thr

<210> SEQ ID NO 3
<211> LENGTH: 29
<212> TYPE: PRT
<213> ORGANISM: Artificial Sequence
<220> FEATURE:
<223> OTHER INFORMATION: synthetic peptide
```

```
<400> SEQUENCE: 3

Ser Leu Gly Ala Glu Gln Arg Thr Glu Ser Ile Ile His Arg Ala Leu
1               5                   10                  15

Tyr Tyr Asp Leu Ile Ser Ser Pro Asp Ile His Gly Thr
            20                  25

<210> SEQ ID NO 4
<211> LENGTH: 25
<212> TYPE: PRT
<213> ORGANISM: Artificial Sequence
<220> FEATURE:
<223> OTHER INFORMATION: synthetic peptide

<400> SEQUENCE: 4

Glu Gln Arg Thr Glu Ser Ile Ile His Arg Ala Leu Tyr Tyr Asp Leu
1               5                   10                  15

Ile Ser Ser Pro Asp Ile His Gly Thr
            20                  25

<210> SEQ ID NO 5
<211> LENGTH: 20
<212> TYPE: PRT
<213> ORGANISM: Artificial Sequence
<220> FEATURE:
<223> OTHER INFORMATION: synthetic peptide

<400> SEQUENCE: 5

Ser Leu Gly Ala Glu Gln Arg Thr Glu Ser Ile Ile His Arg Ala Leu
1               5                   10                  15

Tyr Tyr Asp Leu
            20

<210> SEQ ID NO 6
<211> LENGTH: 18
<212> TYPE: PRT
<213> ORGANISM: Artificial Sequence
<220> FEATURE:
<223> OTHER INFORMATION: synthetic peptide

<400> SEQUENCE: 6

Glu Gln Arg Thr Glu Ser Ile Ile His Arg Ala Leu Tyr Tyr Asp Leu
1               5                   10                  15

Ile Ser

<210> SEQ ID NO 7
<211> LENGTH: 29
<212> TYPE: PRT
<213> ORGANISM: Artificial Sequence
<220> FEATURE:
<223> OTHER INFORMATION: synthetic peptide

<400> SEQUENCE: 7

Ser Leu Gly Ala Glu His Arg Thr Glu Ser Val Ile His Arg Ala Leu
1               5                   10                  15

Tyr Tyr Asp Leu Ile Thr Asn Pro Asp Ile His Ser Thr
            20                  25

<210> SEQ ID NO 8
<211> LENGTH: 20
<212> TYPE: PRT
<213> ORGANISM: Artificial Sequence
<220> FEATURE:
<223> OTHER INFORMATION: synthetic peptide
```

<400> SEQUENCE: 8

Ser Leu Gly Ala Glu His Arg Thr Glu Ser Val Ile His Arg Ala Leu
1               5                   10                  15

Tyr Tyr Asp Leu
            20

<210> SEQ ID NO 9
<211> LENGTH: 418
<212> TYPE: PRT
<213> ORGANISM: Homo sapiens

<400> SEQUENCE: 9

Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
                20                  25                  30

Pro Asp Ser Thr Gly Ala Leu Val Glu Glu Asp Pro Phe Phe Lys
            35                  40                  45

Val Pro Val Asn Lys Leu Ala Ala Val Ser Asn Phe Gly Tyr Asp
50                  55                  60

Leu Tyr Arg Val Arg Ser Ser Thr Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
                115                 120                 125

Val Thr Ala Pro Gln Lys Asn Leu Lys Ser Ala Ser Arg Ile Val Phe
            130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
                180                 185                 190

Ala Arg Ser Thr Lys Glu Ile Pro Asp Glu Ile Ser Ile Leu Leu Leu
                195                 200                 205

Gly Val Ala His Phe Lys Gly Gln Trp Val Thr Lys Phe Asp Ser Arg
            210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
                260                 265                 270

Ser Ile Ile Phe Phe Leu Pro Leu Lys Val Thr Gln Asn Leu Thr Leu
            275                 280                 285

Ile Glu Glu Ser Leu Thr Ser Glu Phe Ile His Asp Ile Asp Arg Glu
            290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

-continued

```
Leu Phe Asp Ser Pro Asp Phe Ser Lys Ile Thr Gly Lys Pro Ile Lys
            340             345             350

Leu Thr Gln Val Glu His Arg Ala Gly Phe Glu Trp Asn Glu Asp Gly
        355             360             365

Ala Gly Thr Thr Pro Ser Pro Gly Leu Gln Pro Ala His Leu Thr Phe
    370             375             380

Pro Leu Asp Tyr His Leu Asn Gln Pro Phe Ile Phe Val Leu Arg Asp
385             390             395             400

Thr Asp Thr Gly Ala Leu Leu Phe Ile Gly Lys Ile Leu Asp Pro Arg
                405             410             415

Gly Pro
```